United States Patent [19]

Day et al.

[11] Patent Number: 4,851,240

[45] Date of Patent: Jul. 25, 1989

[54] PROCESS FOR RETARDING BACTERIAL GROWTH IN SILAGE

[75] Inventors: Carol A. Day; Brian W. Holton, both of Worcestershire, Great Britain

[73] Assignee: Microbial Developments Limited, United Kingdom

[21] Appl. No.: 189,967

[22] Filed: May 4, 1988

[30] Foreign Application Priority Data

May 7, 1987 [GB] United Kingdom ................ 8710795

[51] Int. Cl.$^4$ .............................................. A23K 3/00
[52] U.S. Cl. ...................................... 426/53; 426/54; 426/61; 426/636
[58] Field of Search ................... 426/36, 61, 321, 334, 426/335, 531, 532, 18, 53, 54, 635, 636

[56] References Cited

U.S. PATENT DOCUMENTS

| | | | |
|---|---|---|---|
| 4,262,023 | 4/1981 | Eddy et al. | 426/36 |
| 4,554,165 | 11/1985 | Richardson | 426/36 |
| 4,621,058 | 11/1986 | Reddy | 426/36 |

*Primary Examiner*—Marianne Cintins
*Attorney, Agent, or Firm*—Ostrolenk, Faber, Gerb & Soffen

[57] ABSTRACT

The use of bacteriophages for controlling unwanted fermentation of food-stuffs, especially silage and cheese, by bacteria is disclosed.

8 Claims, No Drawings

PROCESS FOR RETARDING BACTERIAL GROWTH IN SILAGE

The present invention relates to preparations for the prevention and treatment of microbial infestations in human and animal food-stuffs.

Human and animal food-stuffs are susceptible to a wide variety of microbial infestations. These are rarely beneficial and frequently harmful. Those of a harmful nature can cause mild tainting of the food-stuff, or illness ranging from mild stomach ache to death in the consumer, always assuming that the food is not rendered completely inedible.

Very few forms of infestation are likely to lead to death, but one well known example is Salmonella infection of canned products. Other harmful infestations are generally of a less serious nature but, nevertheless, spoil the product. An example of this kind is Clostridium infection, which can affect both human and animal feeds. Milk products are particularly prone to infection, especially cheese, and the result is an unpleasant acid taste combined with uncontrolled gas production, which may also cause an unsightly, deformed product.

Forage, such as grass, maize, lucerne, arable, beans and peas, is harvested by farmers during the warmer months of the year and conserved by a technique known as ensiling, whereby the material is contained and air is excluded to promote anaerobic fermentation of the sugars present in the fodder to lactic and other beneficial silage acids. The fodder is, thus, preserved as a satisfactory feed for ruminant livestock during the colder months of the year when fresh fodder is not available.

The preserved forage (silage) forms an important part of livestock feeding regimes in the economic production of milk and meat by farmers. Consequently, it is important that as much as possible of the original nutritional content be preserved, and to reduce to a minimum infection and deterioration caused by spoilage micro-organisms during ensiling. Such infection is unlikely if the ensiling is performed under ideal conditions.

However, silages clamped under less-than-perfect conditions are prone to secondary fermentation by spoilage micro-organisms, particularly when the acid level is insufficient to stabilise the silage, the silage temperature is raised, the dry matter content is low, nitrate levels in the silage are high, or if soil and slurry have contaminated the silage through poor harvesting conditions.

Owing to the unpredictability of weather conditions and the necessity of setting up clamps at times dictated by other controlling factors, ideal conditions for silage-making are only rarely attainable.

Secondary fermentation in silage is frequently characterised by the proliferation of Clostridium species such as *C. tyrobutyricum* and *C. sporogenes* (so-called butyric acid bacteria) which cause breakdown of protein and residual sugars to butyric acid and ammonia, thereby significantly reducing the nutritional value of the silage and reducing edibility.

Listeria can also infect silages, especially those which are prone to aerobic deterioration. Such silages include those which are badly consolidated and therefore allow ingress of air; those which are susceptible to surface ingress of air from possible poor clamp management with inadequate plastic sheeting practice; and bale silages having high dry matter content and, hence, low consolidation, and which are also prone to plastic bag damage, allowing easy access of air and subsequent growth of Listeria spp.

Significant association of the feeding of poor or mouldy silage with the incidence of listeriosis in livestock is well reported. Use of Listeria specific phages serves to reduce the incidence of listerioris and listeric abortion in cattle and sheep. Although rarely observed, Listeria spp. are also pathogenic to humans.

In order to prevent such secondary fermentation, modern methods of silage production involve the use of silage additives before ensiling. Traditional additives are based on acids such as formic, sulphuric and hydrochloric acids, and function by directly acidifying the forage to inhibit spoilage micro-organisms.

Adding acids directly to forage during harvesting can be a hazardous procedure for farm workers, and can cause corrosion in farm machinery. More recently, biologicals have been used as silage additives. For example, preparations containing one or more strains of homofermentative lactic acid bacteria are added to forage, accelerating fermentation and increasing levels of natural silage acids, thus helping to preserve the silage.

Many biological silage additives also contain enzymes capable of hydrolysing fibrous components in the forage to increase the levels of sugars available for fermentation. The use of such enzymes is generally preferred for those forages with a low natural sugar content and which might otherwise not support production of sufficient lactic acid.

An alternative method of protection involves treating the raw crop with a light solution of a combination of formaldehyde and formic acid. The main disadvantage of this method is that formaldehyde is not only a protein cross-linking agent but also a carcinogen.

Recent research has led to the use of such agents as molasses and enzymes to protect the crop. These methods are costly, and many workers are currently engaged in research to find a cheaper, effective method for protecting silage.

In other areas, microbial infestation need not always be undesirable. Production of certain cheeses, for example, is totally reliant on the presence of certain microbes, and yoghurt is a thick culture of harmless bacteria.

Bacterial cultures are also of use in their own right and are becoming increasingly important with recent break-throughs in biotechnology. However, such cultures become useless if contaminated by virus (bacteriophage, or phage).

Phages were first recognised in the early 1960's. Since then, attention has been focussed on them for two reasons; their effect on the bacterial cell and their ability, in some instances, to translocate bacterial genes. This latter ability is particularly important to present day genetic studies and has enabled the development of useful gene cloning techniques. Phages are, nevertheless, being superseded by other systems less likely to damage the organisms concerned. Cultures infected by uncontrolled phage are useless, as no means are available to combat virus infection. Such cultures can only be destroyed.

It has now been discovered that the treatment of food-stuffs with small amounts of phage can prevent infestation by harmful microbes.

Thus, in a first aspect of the present invention, there is provided the use of at least one species of bacteriophage in the treatment or prevention of bacterial infection in food-stuffs or their ingredients.

In an alternative aspect of the present invention, there is provided a process for the preparation of a human or animal food-stuff comprising the addition of a preparation of at least one species of bacteriophage to the food-stuff or at least one of the ingredients therefor.

The present invention also provides preparations containing at least one variety of bacteriophage and a suitable carrier therefor for use according to either of the above described aspects of the present invention.

Particular advantages of the present invention lie in the non-corrosive qualities of the preparations, effective ensiling of wet, low-sugar grass, and that there is less effluent and spoilage, leaving more silage as feed.

Bacteriophages are highly host-specific. Extremely rapid multiplication within the host cell occurs leading to the destruction of the cell (lysis) and the release of up to 20,000 new phages, each capable of further infection. Phages are essentially non-living outside the host cell and, therefore, can exhibit very considerable longevity, making them particularly useful in preparations according to the present invention.

It will be appreciated that as bacteriophages are highly specific in the organisms they can infect, any one variety of phage will only infect one species of bacterium and, frequently, only selected strains of that species. There is thus no danger to the consumer of being infected by the phage.

A particular advantage in the use of phages according to the present invention is that, with only extremely small quantities of phase being required for efficacy, there is no adverse effect on flavour. Furthermore, as phages only infect highly specific organisms, no propagation of phage can take place in the absence of the host bacterium, so the food-stuff remains completely unaffected by their presence.

A disadvantage of previous antimicrobial preparations was the lack of any specificity of attack. Any antibiotic treatment resulted in the indiscriminate elimination of the natural bacterial flora, not only of the food-stuff, but also in the gut of the consumer. Again, phages provide the solution to this problem and can be selected against any bacterium as required.

Thus, in a further aspect of the present invention there is provided the use or process as defined above wherein the bacteriophage(s) is selected according to host bacterium specificity.

It will be appreciated that, while lysogenic phages can be used in accordance with the invention, the use of lytic phages is generally preferred, as infection results in the rapid destruction of the host.

Bacteria are known to be able to develop resistance to phage infection. The present invention, therefore, further provides a use or process as described above wherein the preparation comprises at least two strains of phage specific for one host. If the target micro-organism develops a resistance to one phage, or the phage becomes lysogenic, elimination of the unwanted organism still occurs.

Still more preferable is the 'rotation' of phages. For example, in the case where three phages are available against Clostridia spp., then three preparations of different phage pairs are available for use in successive treatments to minimise the risk of resistance developing.

As used herein, 'rotation' means varying the bacteriophage composition of preparations according to the present invention with different batches of food-stuff prepared in the same locale. Such variation need not be cyclical, or even regular, provided that different compositions are used occasionally to prevent resistance developing.

Preparations according to the present invention may contain phages specific for several different species of bacterium. A silage treatment may contain phages specific for *C. sporogenes, C. tyrobutyricum* and Listeria spp., for example.

In a preferred embodiment, the present invention provides a silage additive containing bacteriophages specific to those Clostridium species most commonly found in silages, either alone or on a carrier or base, or combined with lactic acid bacteria and/or hydrolytic enzymes, and/or combined with other silage additive constituents at a bacteriophage concentration of $10^2$ to $10^{12}$ pfu (plaque forming units) per gram of forage.

Clostridia spp. are particularly susceptible to treatment according to the present invention. Anaerobes are generally significantly less efficient than aerobes, as life processes must be restricted to essentials to allow effective exploitation of the anaerobic environment. Thus, the highly sophisticated mechanisms of the likes of *E. coli* are unavailable to anaerobes to generate a defence against phage attack.

A further advantage accrues from silage treated with Clostridium-specific phage. Cellulose for example, is not available as a source of nutrition to humans, but can be digested by ruminants through the services of their gut flora. Three main types of flora are recognised and are generally referred to by the chemical intermediates they generate; butyric, propionic and acetic acids. The butyric acid pathway is considerably more inefficient than either of the other two, and the flora concerned are generally Clostridia spp. Thus, silage treated with Clostridium-specific phage is not only preserved from clostridial degradation, but also transmits the phage to the recipient ruminant. This destroys the clostridial flora in the rumen, allowing the animal to make more efficient use of its food. Direct treatment with phage preparation(s) would also have the same effect and, as such, forms a further aspect of the present invention.

Thus, a use or process as described above is effective not only as a food preservative but also as a growth promoter for livestock, by causing more efficient utilisation of nutrients.

Addition of specific clostridial phage ($10^5$–$10^7$ pfu/ml) to drinking water and/or feedingstuffs will control butyric acid metabolism in the rumen, leading to useful weight gain (and milk production in cattle). Furthermore, for cattle treated both with augmented silage and direct administration, a compound effect is likely to be observed as, not only is there a better fermentation of the silage itself, so increasing nutritive value, but also an effect on milk production/weight gain is likely, through carry-over of phage in the silage into the rumen and subsequent compound effects from rumen manipulation.

Suitable bacteriophages for use according to the present invention may be isolated from soils, silages, silage effluents and farm slurry, animal and plant wastes, alimentary tract contents, air or water, preferably using known bacteriophage enhancement techniques [c.f. Betz, J. V., & Anderson, K. E., (1983), J. Bact., 87, 408]. Bacteriophages so isolated may be chaaracterised as to their host specificity by known techniques.

Suitable quantities of phage for use according to the present invention may be obtained, for example, by a batch technique, wherein a culture of host bacterium is grown nearly to capacity and then seeded with phage. After a suitable time has elapsed to allow maximal phage propagation, the culture is further lysed by chemical or physical techniques, if required, and the lysate spun down. The phage-bearing supernatant may then be further purified, for example by ultrafiltration, and concentrated (freeze-drying, for instance). The resulting preparation can be used directly or further combined with other ingredients to aid in packaging, end-use etc.

Large-scale commercial production of Clostridium-specific phages may involve initial anaerobic fermentation of the of host Clostridium species, preferably in optimal submerged culture conditions for a time adequate to achieve logarithmic growth of the culture. Specific phage preparations are then introduced to the clostridial culture and incubation continued until maximal lysis can be demonstrated. Downstream recovery of such a phage preparation from solution may be effected by initial low-speed centrifugation to remove any remaining bacterial cells and debris, and the phage purified and concentrated by ultracentrifugation and ultrafiltration techniques. The resulting concentrated phage preparation can be cryoprotected and freeze-dried by techniques well-known in the art, or preferably plated onto, or mixed with, a suitable carrier material and air- or vacuum-dried as appropriate. Bacteriophages can also be encapsulated in acid-resistant biodegradable gums to provide a composite silage additive product optionally containing organic acids. Typical activity levels of phages prepared according to the above methods range from $10^9$–$10^{12}$ pfu/gram of concentrate according to the particular phage morphology.

When used to preserve silage, a suitable preparation according to the invention contains from $10^2$–$10^{10}$ pfu/g, preferably $10^5$–$10^7$/g. The preparation is conveniently a liquid and is sprayed onto the crop during clamping, although any other suitable technique may be used.

Preparations according to the present invention suitably contain at least two varieties of phage, optionally specific for more than one family of bacterium, as required. The preparations may be liquid or solid according to requirements. Liquid preparations are suitable for use in the preparation of cheese, spraying on silage, or administration to livestock, and may be simple suspensions of phage in water, but preferably further comprise a suitable carrier. Suitble carriers may, for example be sugar-based, such as mannitol, but may comprise any suitable substance known in the art.

Liquid preparations may be prepared from any of the preparations generally available for similar use, a suitable quantity of phage being added. In the alternative, a more concentrated 'stock' solution may be prepared for addition to existing commercial products.

Similar considerations to the above apply, *mutatis mutandis*, to solid preparations and formulations for administration to livestock. Solid preparations are usually available in powdered or granular form, and so any 'stock' solution must comprise a carrier, such as ground maize, bran or limestone.

Preparations for the preservation of silage are usefully combinations with the biological-type preparations of the art. Thus, for example, they will contain enzymes and lactic acid bacteria to further enhance the quality of the silage and give the preparations wider applicability.

Formulations for administration to livestock will usually be formulated for inclusion with the feed or addition to drinking water. As a rule, solid formulations are suitable for addition to fodder, while liquid formulations are suitable for addition to drinking water.

Formulations for administration to livestock may also be given directly in any suitable form, such as bolus, capsule, tablet or solution.

In order to determine phage activity in the final product, as well as during preparation, total specific phage counts may be undertaken using, for example, the double gear layer plating technique for plaque production, employing the host microbial species in each case. The method described by Adams, M. H., in "Bacteriophages" (Interscience Publishers (1959)) is suitable for this purpose.

To preserve cheeses from infection, a suitable phage preparation may be added during the cheese-making process, generally at an early stage such as the rennet stage, while the mix is still liquid, to permit even dispersion throughout the cheese. This prevents small pockets of infection from occurring and spoiling the flavour, texture and appearance of the product.

The following Examples are for illustration purposes only, and are not intended to limit the scope of the present invention in any way.

EXAMPLE 1

Preparations

| | Formulated to add per gram of forage |
|---|---|
| Prepared bacteriophage lytic to *Clostridium sporogenes* strains commonly found in silage | $10^6$ pfu |
| Prepared bacteriophage lytic to *Clostridium tyrobutyricum* strains commonly found in silage | $10^6$ pfu |
| Prepared bacteriophage lytic to *Clostridium bifermentans* strains commonly found in silage | $10^6$ pfu |

Granular or soluble based carrier to provide for a manageable application rate to achieve satisfactory distribution into forage, e.g., 500 grams per tonne of forage for dry powder application, or suitably dissolved in water to spray at 1–2 liters per tonne of forage.

EXAMPLE 2

Preparations

Preparations were prepared as in Example 1, with the addition of viable lactic acid bacteria;

| | Formulated to add per gram of forage |
|---|---|
| *Lactobacillus plantarum* | $3 \times 10^5$ cfu |
| *Pediococcus acidilactici* | $1 \times 10^5$ cfu |

EXAMPLE 3

Preparations

Preparation was as in Examples 1 or 2, with the addition of enzymes:

|  | Formulated to add per gram of forage |
|---|---|
| Hemicellulase preparation | 5 xylanase units |
| Polygalacturonase | 2 PG units |
| Microbial cellulase | 2 CMC units |

EXAMPLE 4

Alternative Preparation

|  | Formulated to add per gram of forage |
|---|---|
| Prepared bacteriophage lytic to Clostridium tyrobutyricum strains commonly found in silage | $10^5$ pfu |
| Prepared bacteriophage lytic to Clostridium sporogenes strains commonly found in silage. | $10^5$ pfu |
| Prepared bacteriophage lytic to Clostridium bifermentans strains | $10^5$ pfu |
| Cane or Beet Molasses | 0.009 grams |

EXAMPLE 5

Alternative Preparation

|  | Formulated to add per gram of forage |
|---|---|
| Prepared bacteriophage lytic to Clostridium tyrobutyricum strains commonly found in silage | $10^6$ pfu |
| Prepared bacteriophage lytic to Clostridium sporogenes strains commonly found in silage | $10^5$ pfu |
| Prepared bacteriophage lytic to Clostridium bifermentans strains commonly found in silage All suitably acid protected | $5 \times 10^4$ pfu |
| Formic acid (85%) | 0.002 ml |

EXAMPLE 6

FIELD TRIALS 60-tonne capacity silage clamps were randomly filled with field-cut ryegrass treated at pick-up with the following silage additive compositions:

A. Without an additive;

B. With a conventional acid-based additive (formic acid) at an application rate of 2 liters per tonne of forage;

C. With a conventional biological silage additive (SAFE-SILE liquid (registered trade mark)) at an application rate of 2 liters per tonne of forage;

D. With an additive containing a clostridial bacteriophage preparation adapted to give a concentration of $10^5$ pfu per gram of forage; and E. With an additive containing a conventional biological silage additive (SAFE-SILE liquid) combined with a clostridial bacteriophage preparation to give a concentration of $10^7$ pfu per gram of forage.

Results are shown in Table 1.

TABLE 1

|  | Time | DM | pH | NH$_3$N | CP | MAD | D | ME | DCP | LACT | ACET | BUT |
|---|---|---|---|---|---|---|---|---|---|---|---|---|
| A | 3 wks | 30.1 | 4.40 | 7 | 16.8 | 33.4 | 64.3 | 10.3 | 113 | 0.83 | 0.10 | 0.37 |
|  | 9 wks | 27.4 | 4.85 | 12 | 15.7 | 33.0 | 64.5 | 10.3 | 105 | 0.77 | 0.10 | 0.60 |
| B | 3 wks | 28.6 | 4.25 | 2 | 20.1 | 30.6 | 66.6 | 10.6 | 141 | 0.67 | 0.39 | 0.31 |
|  | 9 wks | 26.7 | 4.85 | 14 | 15.4 | 36.4 | 61.9 | 9.9 | 103 | 0.29 | 0.10 | 0.55 |
| C | 3 wks | 32.9 | 3.90 | 5 | 16.7 | 36.0 | 62.2 | 9.9 | 113 | 1.70 | 1.80 | 0.10 |
|  | 9 wks | 34.7 | 3.95 | 7 | 16.0 | 33.2 | 64.5 | 10.3 | 107 | 1.37 | 0.10 | 0.12 |
| D | 3 wks | 30.5 | 4.20 | 5 | 16.5 | 33.0 | 64.7 | 10.3 | 112 | 1.72 | 1.58 | 0.10 |
|  | 9 wks | 31.8 | 4.25 | 7 | 17.5 | 31.7 | 65.7 | 10.5 | 120 | 1.47 | 0.10 | 0.10 |
| E | 3 wks | 31.4 | 3.70 | 4 | 17.4 | 31.6 | 65.8 | 10.5 | 119 | 1.82 | 0.32 | 0.27 |
|  | 9 wks | 32.2 | 3.70 | 6 | 15.8 | 32.7 | 64.9 | 10.3 | 106 | 3.50 | 0.10 | 0.10 |

Silage analyses were taken at regular intervals to assess: dry matter (DM%); pH; ammonia-nitrogen (NH$_3$N as % of total nitrogen); crude protein (CP%); modified acid detergent fibre content (MAD%); D value (%); metabolisable energy (ME MJ/kg); digestable crude protein (DCP g/kg) and volatile (lactic, acetic and butyric) fatty acids (% wet basis) by gas liquid chromatography.

The D value is a measure of the digestibility of the silage, higher values being indicative of better digestibility. For grass, the D value is calculated according to the following equation:

$$D = 91.4 - (0.81 \times MAD).$$

Silages treated with bacteriophage preparations showed more favourable levels of ammonia nitrogen and butyric acid which were indicative of secondary fermentation inhibition.

EXAMPLE 7

Field Trials 600-tonne capacity silage clamps were randomly filled with field-cut rye grass treated at pick-up with the following silage additive compositions:

A. Without an additive; and

B. With an additive containing a conventional biological silage additive (SAFE-SILE liquid, Downland Marketing Ltd.) combined with a clostridial bacteriophage preparation to give a concentration of $10^5$ pfu per gram of forage.

Results are shown in Table 2.

TABLE 2

|  | Time | DM | pH | NH$_3$N | CP | MAD | D | ME | DCP | LACT | ACET | BUT |
|---|---|---|---|---|---|---|---|---|---|---|---|---|
| A | 4 wks | 18.6 | 3.95 | 7 | 16.7 | 32.3 | 65.2 | 10.4 | 113 | 1.47 | 0.41 | 0.28 |
|  | 13 wks | 16.5 | 4.55 | 13 | 13.0 | 41.2 | 58.0 | 9.2 | 82 | 0.96 | 1.42 | 0.35 |
| B | 4 wks | 17.4 | 3.80 | 6 | 16.1 | 33.8 | 64.0 | 10.2 | 108 | 1.61 | 0.10 | 0.10 |
|  | 13 wks | 18.3 | 4.10 | 9 | 14.9 | 35.3 | 62.8 | 10.0 | 98 | 2.47 | 1.23 | 0.25 |

As before, silage analyses were taken at regular intervals to assess dry matter (DM%), pH, ammonia-nitrogen (NH₃N as % of total nitrogen), crude protein (CP%), modified acid detergent fibre content (MAD%), D value (D%), metabolisable energy (ME MJ/kg), digestible crude protein (DCP g/kg) and volatile (lactic, acetic and butyric) fatty acids (% wet basis) by gas liquid chromatography.

Again, silages treated with bacteriophage preparations showed more favourable levels of ammonia nitrogen and butyric acid indicative of secondary fermentation inhibition.

EXAMPLE 8

Toxicology (1) Toxicological Trials on Single Dairy Cows

Two pedigree Friesian dairy cows in first lactation period (Registration Nos: 6190154 and 5958858) from the Microferm herd were isolated and acclimatised for 10 days pre-trial. Milk samples during this period were analysed and found not to contain specific clostridial bacteriophages.

Cow No. 6190154 was administered through drinking water a bacteriophage preparation specific to *Clostridium sporogenes* at a dose level of $10^{14}$ pfu/cow/day for 14 days.

Cow No. 5958858 was administered through drinking water a bacteriophage preparation specific to *Clostridium tyrobutyricum* at a dose level of $10^{14}$ pfu/cow/day for 14 days.

These dosage levels are considered to be 100 to 1000-fold increases of bacteriophage ingested compared to those levels ingestible through normal intake of bacteriophage treated silage.

The results are shown in Table 3.

TABLE 3

| Milk Records at Commencement of Trial | | | | |
|---|---|---|---|---|
| | Average daily yield | Butter Fat % | Protein % | Lactose % |
| Total herd (38 cows) | 19.85 | 4.30 | 2.76 | 4.63 |
| 6190154 | 17.20 | 4.10 | 3.06 | 4.73 |
| 5958858 | 17.20 | 4.19 | 3.15 | 4.69 |
| Milk Records at completion of Trial | | | | |
| Total Herd (38 cows) | 20.63 | 4.12 | 2.94 | 4.68 |
| 6190154 | 19.35 | 4.17 | 3.15 | 4.79 |
| 5958858 | 22.66 | 4.20 | 3.19 | 4.53 |

No samples of milk analysed at 3-day intervals for each cow on trial were found to contain specific Clostridial bacteriophage. No effects of treatment were apparent in the cows during or following the trials.

(2) Toxicological Trial in the Rat

A single dose oral toxicity study in the rat was performed. The procedure used met the requirements of the limit test for acute oral toxicity described in Annex V of the EEC Commission Directive relating to the classification, packaging and labelling of dangerous substances. This is an acceptable method in the assessment of additives in animal nutrition.

The test material was a mixture of equal concentration of bacteriophages specific to *Clostridium sporogenes* and to *Clostridium tyrobutyricum* at a combined level of $2 \times 10^{10}$ pfu/gram. This was administered as a single oral dose at a level of 2000 mg/kg live weight. In all cases no effects of treatment were observed and no abnormalities revealed at necropsy on termination of the study.

EXAMPLE 9

Bacteriophage Cheese Preparations

Cheeses are prepared by the normal cheese-making process with addition of clostridial phage mixtures at $10^5$–$10^7$ pfu/ml milk.

The addition of phage takes place at the rennet stage of cheese-making to avoid the heat treatment stage of the milk. This ensures phage viability. Incorporation of phage at the rennet stage also ensures even distribution of phage during formation of the curds, so that it is not entirely lost in the whey (usually drained off).

Thermal resistance of phage is relatively high. Most clostridial phages survive 60° C./80 mins. Heat treatment of milk for cheese-making rarely exceeds 40° C., so phage can be added at any stage. During and following the ripening stage, samples may be taken for phage count and Clostridium counts.

We claim:

1. A method of retarding undesirable bacterial growth in silage which comprises the administration thereto of a retarding bacterial growth effective, nontoxic amount of a bacteriophage.

2. A method according to claim 1 wherein the bacteriophage has specificity for an organism selected from the group consisting of Clostridia spp. and Listeria spp.

3. A method according to claim 1 in which at least two bacteriophages having different specificities are applied.

4. A method according to claim 3 in which at least one of the bacteriophage has specificity for an organism selected from the group consisting of Clostridia spp. and Listeria spp.

5. A method according to claim 1 in which the administration is effected a plurality of times and during at least one such additional administration, a bacteriophage having a different specificity is administered.

6. A method according to claim 1 wherein the bacteriophage is administered to the silage during the preparation thereof.

7. A method according to claim 1 wherein a liquid containing $10^2$ to $10^{10}$ pfu/g bacteriophage is administered to the silage.

8. A method according to claim 7 wherein the liquid contains $10^5$ to $10^7$ pfu/g and bacteriophage is sprayed on the silage.

* * * * *